United States Patent
Herlihy

(10) Patent No.: US 7,354,957 B2
(45) Date of Patent: Apr. 8, 2008

(54) MULTI-FUNCTIONAL THIOXANTHONE PHOTOINITIATORS

(75) Inventor: Shaun Lawrence Herlihy, Chatham (GB)

(73) Assignee: Sun Chemical Corporation, Parsippany, NJ (US)

(*) Notice: Subject to any disclaimer, the term of this patent is extended or adjusted under 35 U.S.C. 154(b) by 0 days.

(21) Appl. No.: 10/492,952

(22) PCT Filed: Sep. 24, 2002

(86) PCT No.: PCT/GB02/04324

§ 371 (c)(1),
(2), (4) Date: Sep. 3, 2004

(87) PCT Pub. No.: WO03/033492

PCT Pub. Date: Apr. 24, 2003

(65) Prior Publication Data
US 2005/0014860 A1 Jan. 20, 2005

(30) Foreign Application Priority Data
Oct. 18, 2001 (GB) ................. 0125098.4

(51) Int. Cl.
C08F 2/46 (2006.01)
C08J 3/28 (2006.01)
C07D 409/12 (2006.01)
C07D 409/14 (2006.01)
C09D 11/10 (2006.01)

(52) U.S. Cl. .................. 522/53; 522/101; 522/103; 522/107; 549/27; 549/28

(58) Field of Classification Search .............. 522/53, 522/904, 905, 101, 103, 107; 549/27, 28
See application file for complete search history.

(56) References Cited

U.S. PATENT DOCUMENTS

| | | | | |
|---|---|---|---|---|
| 4,348,530 A | * | 9/1982 | Kvita et al. .................. 549/27 |
| 4,367,324 A | * | 1/1983 | Zweifel et al. .............. 526/256 |
| 4,418,138 A | * | 11/1983 | Curtis ......................... 430/253 |
| 4,459,416 A | * | 7/1984 | Curtis et al. ................. 549/27 |
| 4,506,083 A | * | 3/1985 | Kvita et al. .................. 549/27 |
| 4,602,097 A | * | 7/1986 | Curtis ......................... 549/27 |
| 6,025,408 A | * | 2/2000 | Williams et al. .............. 522/53 |
| 6,960,668 B2 | * | 11/2005 | Timms et al. ................. 549/27 |
| 2005/0165126 A1 | * | 7/2005 | Herlihy et al. ................ 522/25 |

FOREIGN PATENT DOCUMENTS

ES 2015341 8/1990
WO WO 97/49664 12/1997

OTHER PUBLICATIONS

N.S. Allen et al.; New Trends and Developments in the Photochemistry and Photoinduced Polymerisation Activity of Thioxanthone Initiators; vol. 5; pp. 7-16; 1999.

L. Pouliquen et al.; Macromolecules: Functionalized Polysiloxanes with Thioxanthone Side Groups: A Study of Their Reactivity as Radical Polymerization Macroinitiators; vol. 28; pp. 8028-8034; 1995.

L. Angiolini et al.; Copolymeric Systems with Pendant Thioxanthone and a-Morpholinoacetophenone Moieties as Photosensitizing and Photoinitiating Agents for UV-Curable Pigmented Coatings; Journal of Applied Polymer Science; vol. 55, pp. 1477-1488; 1995.

* cited by examiner

Primary Examiner—Susan W. Berman
(74) Attorney, Agent, or Firm—Dickstein Shapiro LLP

(57) ABSTRACT

Compounds of formula (I): {where n is a number from 1 to 6; $R^3$ is hydrogen, methyl or ethyl; A represents a group of formula —[O(CHR$^2$CHR$^1$)$_a$]$_y$—,—[O(CH$_2$)$_b$CO]$_y$—, or —[O(CH$_2$)$_b$CO]$_y$—,—[O(CHR$^2$CHR$^1$)$_a$]-(where one of $R^1$ and $R^2$ is hydrogen and the other is hydrogen, methyl or ethyl); a is from 1 to 2; b is from 4 to 5; y is from 3 to 10, Q is a residue of a polyhydroxy compound having 2 to 6 hydroxy groups; and x is greater than 1 but no greater than the number of available hydroxyl groups in Q} and esters thereof are useful as photoinitiators for the preparation of energy-curable compositions, such as printing inks

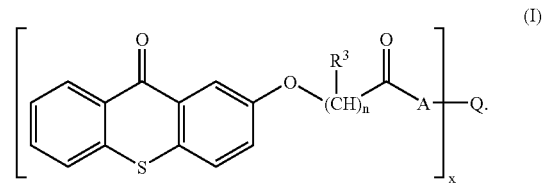

(I)

16 Claims, No Drawings

MULTI-FUNCTIONAL THIOXANTHONE PHOTOINITIATORS

The present invention relates to a series of novel compounds based on thioxanthone, which are useful as multi-functional photoinitiators, and which may be used in various coating compositions, including varnishes, lacquers, printing inks and the like, especially printing inks. The invention also provides radiation-curable surface coating compositions which include at least one of the compounds of the present invention as a photoinitiator.

The compounds of the present invention comprise a polymeric core based on a polyhydroxy polymeric compound which is chemically bonded to two or more groups derived from thioxanthone or an analogue thereof.

Photoinitiators used in energy-curable surface coating formulations need to have good cure speed, and particularly good surface curing activity, low odour and good solubility. Moreover, as consumers become increasingly wary of extraneous compounds in foodstuffs, in order to comply with likely future legislation, the tendency of the compounds to migrate and be extracted should also be low.

Furthermore, in order for the compounds to be useful in practice, it is necessary that they should be preparable with ease and economically on a commercial scale. Thus, one requirement is that, in the course of preparation of the compounds, the reaction rates should be relatively fast. It is becoming increasingly difficult to meet all of these requirements.

In recent years, thioxanthone derivatives, particularly isopropylthioxanthone and diethylthioxanthone, have been extensively used in UV curable printing ink applications. However, these are not entirely satisfactory because, following curing, unreacted thioxanthone derivatives of this type have a tendency to migrate from printing inks into, for example, packaged foodstuffs.

However, thioxanthone and many of its derivatives are potentially very valuable as photoinitiators, since they show two absorption peaks, which are in areas of strong UV emission from medium pressure mercury lamps and results in good through curing, a property particularly valuable in printing inks. There is, therefore, a need for compounds which share the advantages of thioxanthone but which do not migrate to the same extent.

Simple thioxanthone derivatives, such as isopropylthioxanthone, are solids at room temperature with only limited solubility in printing inks, making them difficult to incorporate directly. As a result, they are generally added to the formulation as a liquid blend with other photoinitiators and amine synergists, to provide the right balance of properties, price and ease of use. Thioxanthone itself is highly insoluble in printing inks and in most common organic solvents.

Photoinitiator reactivity per gram is very important in curing. If a material is less reactive than desired, it can be added at higher levels to maintain the cure speed of a formulation but only to a limited extent. Above a concentration of 10-12% non-acrylate functional materials either start to behave as plasticisers, as in the case of many aminoacrylate synergists, or just reduce the crosslink density of the cured film to a point where its mechanical properties are impaired. This effect can be countered to some extent by using high functionality acrylate monomers, such as di-pentaerythritol pentaacrylate, to increase the crosslink density, but costs will rise dramatically and formulation flexibility will be lost if this approach is taken.

The tendency of Type II (hydrogen abstraction) photoinitiators to migrate or be extracted from the cured film is in theory higher than for Type I (cleavage) photoinitiators. This is because cleavage photoinitiators generate two highly reactive free radicals which tend to be bound into the cured film by reacting with an acrylate group. Hydrogen abstraction photoinitiators also produce two free radicals in a bimolecular reaction with an amine synergist. Of these, the aminoalkyl radical is highly reactive and binds into the cured film by reacting with an acrylate group, but the ketyl radical has a low reactivity towards acrylate bonds and undergoes termination reactions, or else oxidises back to the ketone. Solvent extraction of a cured film never recovers all of the Type II photoinitiator used, so by whatever mechanism, these materials are capable of becoming bound into the cured film. The tendency to migrate and be extracted can therefore be minimised for both photoinitiator types by increasing the functionality, i.e. by using multifunctional rather than monofunctional photoinitiators.

The tendency of a material to be extracted from a cured film will also depend to some extent on the solvent (simulant) used for the extraction process. Food simulants currently approved in Europe are water (soft drinks and milk), 10% ethanol in water (wine), 3% acetic acid in water (fruit juice) and either olive oil, 95% ethanol in water or isooctane (fatty foods). Since most of these simulants are water based, a photoinitiator should also not be water-soluble in order to achieve the lowest extraction levels. Water insolubility is also important for photoinitiators used in lithographic inks because otherwise they may dissolve in the fount solution and be removed from the ink before the curing stage. Limited water solubility may also disrupt the ink/fount balance, leading to poor printing performance.

WO 97/49664 discloses a series of compounds which may be used as photoinitiators, and some of which include a residue derived from thioxanthone or a derivative thereof. However, the compounds disclosed in WO 97/49664 are mono-functional, which leads to a low functionality per gram and low reactivity. Moreover, they are relatively sensitive to or soluble in water and other aqueous fluids, and so cannot be used in applications where foodstuffs are involved because of their tendency to be extracted. Their water sensitivity or solubility may make them unsuitable for use in lithographic inks.

N. S. Allen et al. [Trends in Photochemistry & Photobiology, Vol. 5, 7-16 (1999)] discusses the properties of a wide variety of thioxanthone derivatives which may be used as photoinitiators, including some which are based on a polymeric backbone. However, these compounds, unlike those of the present invention, have the thioxanthone functional moiety as pendant groups attached by a chain, of varying length, to a polymeric backbone. Such compounds have enormous viscosity and can be used only with great difficulty in coating compositions. Similar compounds are disclosed by Pouliquen et al. [Macromolecules, Vol. 28, 8028-8034 (1995)] and Angiolini et al. [J. Appl. Poly. Sci., Vol. 55, 1477-1488 (1995)] and suffer the same disadvantages.

ES 2 015 341 also discloses a series of compounds in which a thioxanthone system is attached to a polymer chain. In this case, the compounds are monofunctional or are multi-functional but attached as pendant groups to a polymeric backbone.

It can be seen, therefore, that there is a need for a multifunctional photoinitiator which has a high functionality, good solubility in coating formulations, high reactivity and which gives rise to cured coatings which have extremely low odour and are likely to have a much lower tendency to migrate and be extracted than most known alternatives.

We have now discovered a series of multi-functional compounds based on 2-hydroxythioxanthone as a starting material and which meet these requirements. The multifunctional nature of the material keeps the functionality per gram relatively high and the polymeric linking group renders the material highly soluble in coating formulations, especially UV-curable formulations. The product is also a liquid which is compatible with UV curing formulations and gives rise to coatings which have extremely low odour and are likely to have a much lower tendency to migrate and be extracted than most alternatives.

Thus, the present invention consists in photoinitiator compounds of formula

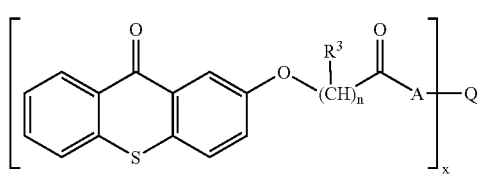

{where:

n is a number from 1 to 6;

$R^3$ represents a hydrogen atom, a methyl group or an ethyl group, and, when n is greater than 1, the groups or atoms represented by $R^3$ may be the same as or different from each other;

A represents a group of formula —[O(CHR$^2$CHR$^1$)$_a$]$_y$—, —[O(CH$_2$)$_b$CO]$_y$—, or —[O(CH$_2$)$_b$CO]$_{(y-1)}$—[O(CHR$^2$CHR$^1$)$_a$]—, where:

one of $R^1$ and $R^2$ represents a hydrogen atom and the other represents a hydrogen atom, a methyl group or an ethyl group;

a is a number from 1 to 2;

b is a number from 4 to 5;

Q is a residue of a polyhydroxy compound having 2 to 6 hydroxy groups; and x is a number greater than 1 but no greater than the number of available hydroxyl groups in Q;

when x is a number greater than 1 but no greater than 2, y is a number from 1 to 10; or when x is a number greater than 2, y is a number from 3 to 10};

and esters thereof.

These compounds are useful as photoinitiators for use in energy, e.g. UV, curable coating compositions, including varnishes, lacquers and printing inks, most especially printing inks.

Accordingly, the present invention also provides an energy curable liquid composition, comprising:
(a) a polymerisable component which is at least one ethylenically unsaturated monomer or oligomer; and
(b) a photoinitiator according to the present invention.

The invention still further provides a process for preparing a cured polymeric composition by exposing a composition of the present invention to radiation, preferably ultraviolet radiation.

For the avoidance of doubt, the numbering system employed for the thioxanthone derivatives is as shown in the following formula (IV):

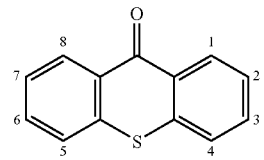

Of these compounds, we prefer those in which n is 1, and particularly those in which n is 1 and $R^3$ represents a hydrogen atom.

Alternatively, when n is a number from 2 to 6, we prefer that one group $R^3$ represents a hydrogen atom, or a methyl or ethyl group and the other or others of $R^3$ represent hydrogen atoms.

In the compounds of the present invention, we prefer that A should represent a group of formula —[O(CHR$^2$CHR$^1$)$_a$]$_y$— where a is an integer from 1 to 2, and y is as defined above, preferably a number from 3 to 10, more preferably a group of formula —[OCH$_2$CH$_2$]$_y$—, —[OCH$_2$CH$_2$CH$_2$CH$_2$]$_y$— or —[OCH(CH$_3$)CH$_2$]$_y$—, where y is as defined above, preferably a number from 3 to 10, or a group of formula —[O(CH$_2$)$_b$CO]$_y$— or —[O(CH$_2$)$_b$CO]$_{(y-1)}$—[O(CHR$^2$CHR$^1$)$_a$]—, where b is a number from 4 to 5 and y is as defined above, preferably a number from 3 to 10. Still more preferably, y is a number from 3 to 6.

Particularly preferred compounds are those in which x is 2 and y is a number from 1 to 10.

It is a feature of the present invention that the compounds are of a generally polymeric nature. The polymeric nature may be provided by either the group represented by Q or the group represented by A or by both.

The polymeric polyhydroxy residue of formula Q-(A-)$_x$, which forms the core of the compounds of the present invention has a major influence on the behaviour of the compounds. In accordance with the present invention, it is important that it should have a polymeric nature, since the resulting compounds tend to be liquid or of low melting point, thus aiding dispersion in the coating composition. Compounds having a similar structure but not polymeric tend to be solid and/or insoluble in these coating compositions. However, we prefer that the core residue, of formula Q-(A-)$_x$, should not have too high a molecular weight, and prefer that the residue of formula Q-(A-)$_x$ should have a molecular weight no greater than 2000, preferably no greater than 1200, still more preferably no greater than 1000, and most preferably no greater than 800.

We particularly prefer that Q should be a residue of ethylene glycol, propylene glycol, butylene glycol, glycerol, trimethylolpropane, di-trimethylolpropane, pentaerythritol or di-pentaerythritol.

When x is a number less than the number of available hydroxy groups in the compound of which Q is the residue, it will be appreciated that the compounds of the present invention may have free hydroxy groups. If desired, or if preparation of the compounds is effected in the presence of an acid, these hydroxy groups may be esterified. There is no particular restriction on the nature of the esters so prepared, although simple, e.g. lower fatty acid, esters are preferred, such as the $C_2$-$C_6$ alkanoyl esters. Examples of such esters include the acetate, propionate, butyrate and valerate esters.

It will be appreciated that, when the compounds of the present invention are analysed, the numbers a, b and y in the above formulae need not be integral, and, indeed, it is unlikely that they will be integral, since the compounds of the present invention may be mixtures of several compounds in which the numbers a, b and y differ. In accordance with the present invention, provided that the average value of each of these numbers is as defined above, this will be satisfactory. Of course, for each individual molecule of the compounds of the present invention, a, b and y will be integral, and it might be possible to separate out such individual compounds, but, in practice, mixtures of these compounds are used.

The compounds of the present invention may be prepared by reactions well known for the preparation of compounds of this type, the exact reaction route chosen depending upon the nature of the compound which it is desired to prepare.

For example, the compounds may be prepared by reacting a 2-carboxyalkoxythioxanthone of formula (II):

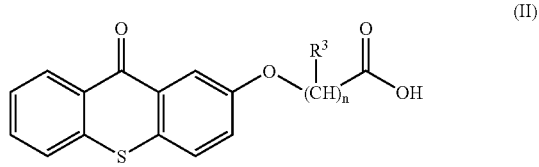

(II)

(in which n and $R^3$ are as defined above), particularly 2-carboxymethoxythioxanthone, with a core compound of formula (III):

(HA)x-Q (III)

where A, x and Q are as defined above.

The reaction is normally and preferably effected in the presence of a solvent, the nature of which is not critical to the present invention, provided that it has no adverse effect on the reagents or on the reaction. Examples of suitable solvents include: aromatic hydrocarbons, such as benzene, toluene or xylene.

The reaction is preferably effected in the presence of an acidic catalyst, for example: a sulphonic acid, such as p-toluenesulphonic acid or methanesulphonic acid; a mineral acid, such as sulphuric, hydrochloric or phosphoric acid; or a Lewis acid, such as aluminium chloride, boron trifluoride or an organotitanate.

The temperature at which the reaction is carried out is likewise not critical to the present invention and may vary widely, depending on the reaction conditions and the nature of the reagents and solvent, provided that it is sufficiently high that the water formed in the course of the reaction is removed, in order to drive the reaction to completion. We therefore generally find it convenient to carry out the reaction at about the reflux temperature of the reaction mixture. The time required for the reaction may also vary widely, depending mainly on the reaction temperature. However, under the preferred conditions outlined above, a period of from 1 to 20 hours will normally suffice.

When the reaction is complete, the desired product may be removed from the reaction mixture by conventional means, for example by washing the reaction mixture, e.g. with water and/or and aqueous alkali, drying and then removing the solvent by evaporation under reduced pressure.

A coating composition incorporating the compounds of the present invention will normally comprise at least one radiation-curable monomer and/or oligomer, the compound of the present invention and possibly an additional reactive diluent. In the case of a printing ink, the composition will also contain a colorant, e.g. a pigment. The radiation-curable monomer or oligomer is preferably an ethylenically unsaturated compound. Examples of suitable acrylate oligomers include aliphatic or aromatic urethane acrylates, polyether acrylates, polyester acrylates and epoxy acrylates (such as bisphenol A epoxy acrylate). Examples of suitable acrylate monomers include hexanediol diacrylate, trimethylolpropane triacrylate, di-trimethylolpropane tetra-acrylate, di-pentaerythritol pentaacrylate, polyether acrylates, such as ethoxylated trimethylol propane triacrylate, glycerol propoxylate triacrylate, ethoxylated pentaerythritol tetraacrylate, and epoxy acrylates such as dianol diacrylate (=the diacrylate of 2,2-bis[4-(2-hydroxyethoxy)phenyl]propane, Ebecryl 150 from UCB) and glycol diacrylates such as tripropylene glycol diacrylate.

Also, the compositions of the present intention preferably contain a synergist, such as an aminoacrylate or a dimethylaminobenzoic acid ester, as is well known in the art. Preferably the synergist will be a dimethylaminobenzoic acid ester in the case of a printing ink or an aminoacrylate in the case of a varnish. Some inks, such as those used in flexographic printing applications may contain both amine types.

The amounts of the radiation-curable monomer or oligomer, photoinitiator, synergist and optional colorant will vary according to the type of varnish or ink, the particular equipment to be used to apply it and the application. However, typically, the amount of photoinitiator plus amine synergist is from 1% to 20% by weight of the total composition.

The multi-functional initiators of formula (I) are especially suited for inks, especially printing inks, including lithographic inks. These typically comprise, as additional components to those referred to above, one or more of pigments, waxes, stabilisers, and flow aids, for example as described in "Printing Ink Manual", fourth edition, Leach R. H. et al. (eds.), Van Nostrand Reinhold, Wokingham, (1988), the disclosure of which is incorporated herein by reference. Since the photoinitiators of the present invention cause yellowing, they may only be used successfully in varnishes if this is not of importance.

The present invention will be further illustrated by reference to the following non-limiting examples. In the formulae given in the Examples, n represents a degree of polymerisation, which may be calculated approximately from the molecular weight (MW) of the compound.

EXAMPLE 1

Preparation of 2-Carboxymethoxythioxanthone

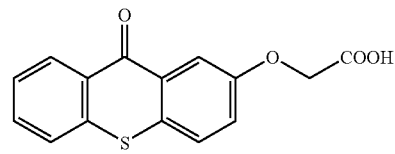

24 g sodium hydroxide was refluxed in 400 ml tetrahydrofuran for five minutes. 22.8 g (0.1 mols) 2-hydroxythioxanthone was added and reflux was continued for 1 hour, during which time the colour changed to bright red, indicating the formation of the sodium salt of 2-hydroxythioxanthone. 35.1 g (0.21 mols) of ethyl bromoacetate was added and reflux was continued for three hours. After cooling to room temperature, 400 ml of deionised water was added, with stirring, and the tetrahydrofuran was distilled out to yield a clear red solution. Reflux was continued for a further 2 hours in order to hydrolyse all the ester intermediate. The solution was then cooled to 50° C., and 400 ml 1.0 M hydrochloric acid was added, with stirring, causing the solid product to precipitate out. After refluxing for a further five minutes to be sure that all the sodium salt was converted to free acid, the solution was cooled to room temperature and stirred for two hours before filtering off the solid, washing with 400 ml deionised water and drying in a vacuum oven at 80° C.

Product yield 28.12 g (97%). Product analysed by NMR.

EXAMPLE 2

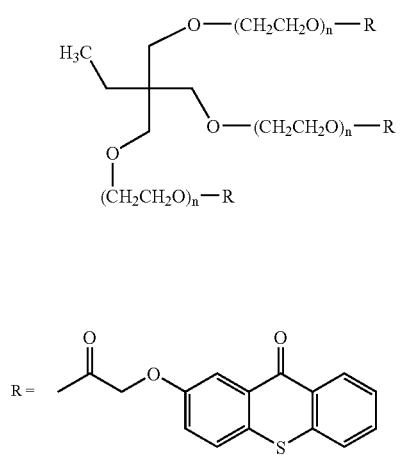

8.58 g (0.03 mols) 2-carboxymethoxythioxanthone and 4.82 g ethoxylated trimethylolpropane (TP70 ex Perstorp) were azeotropically distilled in 200 ml toluene with 0.15 g p-toluenesulphonic acid monohydrate catalyst. After 2.5 hours the solution was cooled, filtered and all solvent was removed on a rotary evaporator to yield a dark red high viscosity oil.

Product analysed by HPLC

EXAMPLE 3

4.5 g (0.01575 mols) 2-carboxymethoxythioxanthone and 1.875 g poly-tetrahydrofuran(250 molecular weight ) were azeotropically distilled in 100 ml toluene with 0.3 g p-toluenesulphonicacid monohydrate catalyst. After 6.5 hours, the solution was cooled, filtered and washed twice with 100 ml 0.25 M sodium hydroxide and twice with a 100 ml deionised water. The organic phase was tried over anhydrous magnesium sulphate and all solvent was removed on a rotary evaporator to yield an orange/red oil.

Product yield 5.67 g (96.2%). Product analysed by HPLC.

EXAMPLE 4

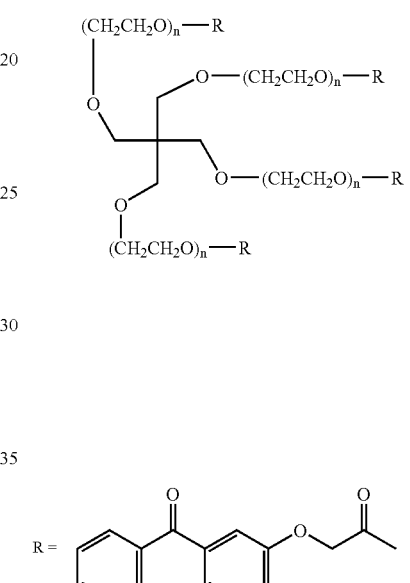

20 g (0.07 mols) 2-carboxymethoxythioxanthone and 9.59 g ethoxylated pentaerythritol (Simusol PTPE ex Seppic) were azeotropically distilled in 300 ml toluene with 0.6 g p-toluenesulphonic acid monohydrate catalyst. After 8.5 hours, the solution was then filtered at 90° C. and washed at 75° C. twice with 200 ml 0.1 M sodium hydroxide and twice with a 200 ml deionised water. The organic phase was azeotropically dried and all solvent was removed on a rotary evaporator to yield a high viscosity orange/red oil.

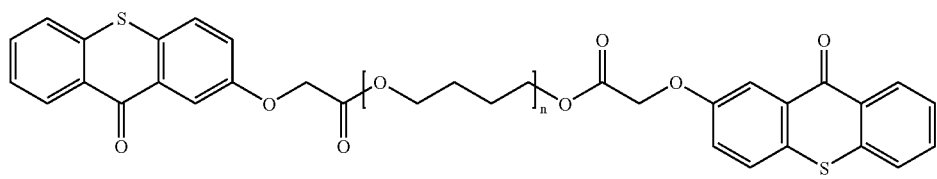

EXAMPLE 5

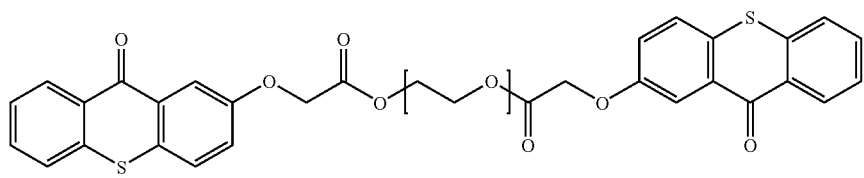

9.0 g (0.0315 mols) 2-carboxymethoxythioxanthone and 2.8 g (0.014 mols) polyethylene glycol (molecular weight 200) were azeotropically refluxed in 100 ml toluene with 0.3 g p-toluenesulphonic acid monohydrate catalyst for a total of 9 hours. This solution was cooled to 60° C. and filtered before removing all solvent on a rotary evaporator to give a dark red high viscosity oil.

Product yield 10.0 g (96.5%). Product analysed by HPLC.

EXAMPLE 6

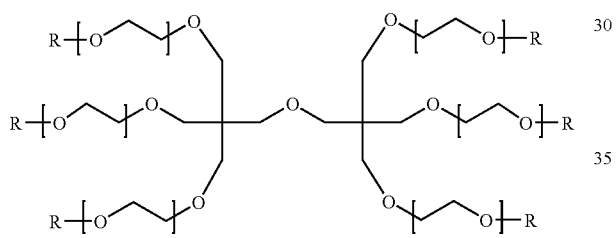

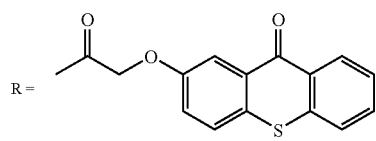

10.0 g (0.035 mols) 2-carboxymethoxythioxanthone and 4.44 g (0.0054 mols) of ethoxylated di-pentaerythritol (DPPI 30 ex Perstorp) were azeotropically refluxed in 100 ml toluene with 0.35 g p-toluenesulphonic acid monohydrate catalyst for a total of 10 hours. The product was insoluble in toluene at low temperature and so the solvent was removed in a rotary evaporator and the product re-disolved in 100 ml dichloromethane and washed twice with 100 ml 0.2 M aqueous sodium carbonate and once with 100 ml deionised water. The solution was dried over anhydrous magnesium sulphate, filtered, and all solvent removed on a rotary evaporator to yield a very high viscosity red oil.

Product yield 7.46 g (56.9%). Product analysed by HPLC.

EXAMPLE 7

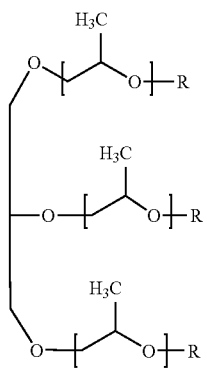

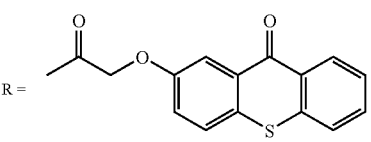

10.0 g (0.035 mols) 2-carboxymethoxythioxanthone and 8.46 g (0.012 mols) of propoxylated glycerol (molecular weight 275) were azeotropically refluxed in 75 ml toluene with 0.3 g p-toluenesulphonic acid monohydrate catalyst for a total of 15 hours. The solution was cooled and filtered before washing twice with 100 ml 0.25 M aqueous sodium carbonate and once with 100 ml deionised water. The solution was dried over anhydrous magnesium sulphate, filtered, and all solvent removed on a rotary evaporator to yield a dark red oil.

Product yield 15.6 g (84%). Product analysed by HPLC.

EXAMPLE 8

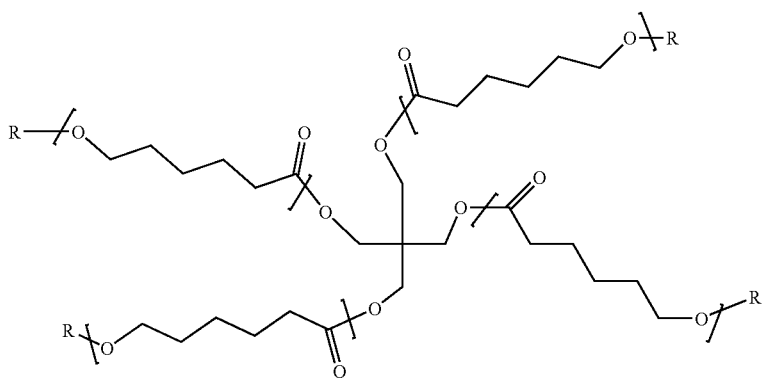

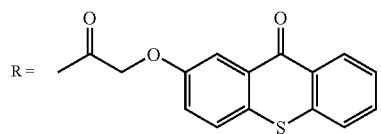

10.0 g (0.035 mols) 2-carboxymethoxythioxanthone and 7.77 g (0.008 mols) of the caprolactone polyol CAPA 4101 ex Solvay were azeotropically refluxed in 75 ml toluene with 0.3 g p-toluenesulphonic acid monohydrate catalyst for a total of 15 hours. The solution was cooled to 90° C. and washed twice with 100 ml 0.5 M aqueous sodium carbonate solution and twice with 100 ml deionised water. The solution was dried by azeotropic distillation before removing all solvent on a rotary evaporator.

Product yield not recorded. Product analysed by HPLC.

EXAMPLE 9

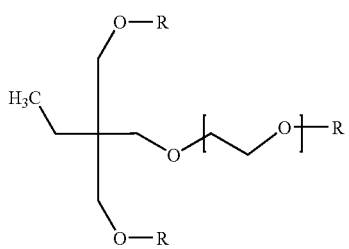

-continued

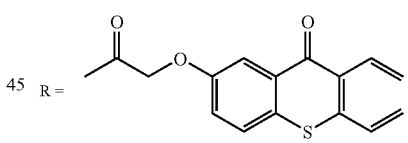

22.6 g (0.0792 mols) 2-carboxymethoxythioxanthone and 10.0 g (0.226 mols) of ethoxylated trimethylol propane (TP70L ex Perstorp) were-azeotropically refluxed for a total of 8 hours under a nitrogen purge in 150 ml toluene with 0.15 g p-toluenesulphonic acid monohydrate catalyst and 0.05 g BHT stabiliser. The product was completely insoluble in the toluene solution and so all solvent was decanted off and the product re-disolved in 200 ml dichloromethane before filtering and washing with 100 ml 10% aqueous potassium carbonate solution and 150 ml deionised water. The solution was dried over anhydrous magnesium sulphate before filtering and removing all solvent on the rotary evaporator to yield a medium viscosity orange oil.

Product yield 10.35 g (37.0%). Product analysed by HPLC.

COMPARATIVE EXAMPLE 1

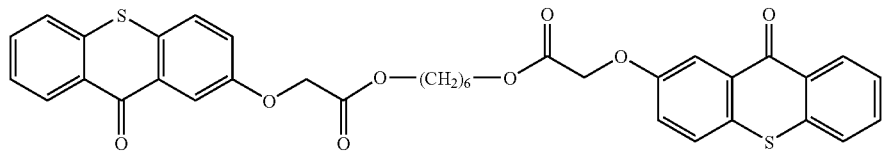

7.15 g (0.025 mols) 2-carboxymethoxythioxanthone and 1.15 g hexane diol (0.01 mols) were azeotropically distilled in 150 ml toluene with 0.3 g p-toluene-sulphonic acid monohydrate catalyst. After 6 hours, the solution was cooled, at which point solid precipitated out of solution. This was filtered off and washed with 0.25 M sodium hydroxide and deionised water before drying in vacuum oven to yield a yellow powder, which was highly insoluble in printing ink formulations.

Product yield 5.37 g (82%). Product analysed by HPLC.

COMPARATIVE EXAMPLE 2

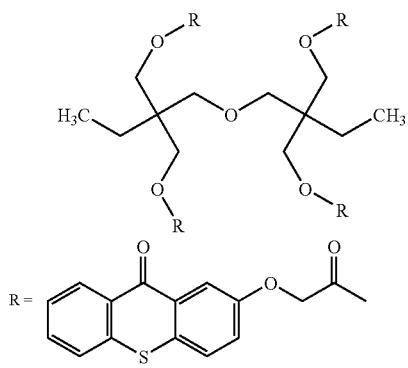

7.15 g (0.025 mols) 2-carboxymethoxythioxanthone and 1.39 g di-trimethylolpropane (0.01 mols) were azeotropically distilled in 150 ml toluene with 0.3 g p-toluenesulphonic acid monohydrate catalyst. After 4.75 hours, the solution was cooled, at which point solid precipitated out of solution. All solvent was removed on a rotary evaporator, and the solid product was re-dissolved in dichloromethane before washing twice with 100 ml 0.25 M sodium hydroxide and twice with 100 ml deionised water. All solvent was removed on a rotary evaporator before drying in a vacuum oven overnight to yield a yellow powder, which was highly insoluble in printing ink formulations.

Product yield 5.9 g (81%). Product analysed by HPLC.

EXAMPLE 10

Evaluation of Initiator in Inks

A cyan pigmented offset ink was prepared based on the following formulation:

| | |
|---|---|
| epoxy acrylate oligomer, CN104 from Cray-Valley | 18% wt |
| Polyester acrylate oligomer, Ebecryl 657 from UCB | 35.7% wt |

-continued

| | |
|---|---|
| Stabiliser, Genorad 16 from Rahn | 0.9% wt |
| Glycerol propoxylate triacrylate (GPTA) | 17.8% wt |
| Irgalite Blue GLO pigment from Ciba | 20.5% wt |
| Photoinitiator blend | 7.1% wt |

The photoinitiator blend comprised:

| | |
|---|---|
| Speedcure MBB ex Lambson | 29.5% wt |
| Rapicure PI507 ex ISP | 48.5% wt |
| Thioxanthone derivative | 22% wt |

The following thioxanthone derivatives were assessed in this formulation (1.562% in the ink):

Isopropyl thioxanthone (Speedcure ITX from Lambson)

2,4-diethylthioxanthone (Speedcure DETX from Lambson)

1,3-dimethyl-2-(2-ethylhexyloxy)thioxanthone (Firstcure LTX from First Chemical)

the product of Example 3

Formulations were printed to a colour density of 1.35 on a cartonboard substrate and cured by passing four times under a 300 W/inch (120 W/cm) medium pressure mercury lamp at 100 m/min. Their relative level of cure was assessed using a combination of scratch resistance, thumb twist and isopropanol rubs tests.

The cure speed in all four experiments was relatively close, but those containing LTX and the product of Example 3 were slightly inferior. Equivalent cure speed was achieved by the addition of 0.31% and 0.23% of LTX and the product of Example 3, respectively. It can be seen that, despite the slightly inferior cure speed compared to ITX and DETX, the product of Example 3 has a reactivity greater than the monomeric thioxanthone derivative LTX. This is particularly encouraging as the product of Example 3 has a lower functionality per gram than ITX, DETX or LTX due to its polymeric nature.

EXAMPLE 11

Photoinitiator Contact Migration Analysis

A cyan pigmented offset ink was prepared based on the following formulation:

| | |
|---|---|
| Epoxy acrylate oligomer, CN104 from Cray-Valley | 18% |
| Polyester acrylate oligomer, Ebecryl 657 from UCB | 35.7% |
| Stabiliser, Genorad 16 from Rahn | 0.9% |

-continued

| | |
|---|---|
| Irgalite Blue GLO pigment from Ciba | 20.5% |
| Glycerol propoxylate triacrylate (GPTA) | 15% |

To this formulation a photoinitiator blend was added comprising;

| | |
|---|---|
| A silicon centered multifunctional photoinitiator, SiMFPI2 from Robinson Brothers Ltd | 55% |
| Aminobenzoate synergist, Rapicure PI507 from ISP | 24% |
| Thioxanthone derivative | 21% |

7.5% of the photoinitiator blend was added to the ink where the thioxanthone derivative was isopropylthioxanthone and 9.0% of the photoinitiator blend was added to the ink where the thioxanthone derivative was that described in Example 3. The ink formulations were then made up to 100% using GPTA. The different photoinitiator blend levels are such that the cure speed of the two inks are equal.

The two ink formulations were printed to a colour density of 1.4 on "Incada Silk 260 gsm" cartonboard substrate from Iggesund using a "Prufbau". The prints were cured at 100 m/min under 2*300 W/inch medium pressure mercury arc lamps operating at full power.

The print samples were then subjected to a contact migration analysis procedure where the cured ink is in contact with either filter paper or polyethylene susceptor and then sandwiched each side by aluminium foil. A number of these sandwiches are arranged in a stack and kept under a pressure of 10 tons for 72 hours in a "Specac".

Where the susceptor is polyethylene this is then soaked for 24 hours in toluene to re-dissolve any migrated photoinitiator. This is then quantified using HPLC and expressed in terms of grams of photoinitiator per unit area of print. Where the susceptor is filter paper a similar procedure is used with acetonitrile in place of toluene.

Levels of photoinitiator contact migration are shown in Table 1.

TABLE 1

Contact migration results for thioxanthone photoinitiators

| Photoinitiator | Contact migration onto paper (mg/m2) | Contact migration onto polyethylene (mg/m2) |
|---|---|---|
| ITX | 1.35 | 1.39 |
| Example 3 | 0.06 | 0.11 |

The results in Table 1 clearly demonstrate that the thioxanthone photoinitiator of Example 3 has a significantly lower tendency to migrate than ITX, the commercial standard thioxanthone photoinitiator.

EXAMPLE 12

Photoinitiator Vapour Phase Migration Analysis

Samples of cured print were prepared as described in Example 11 for the same 2 ink samples. 50 cm$^2$ samples of these were placed in a Petri dish and covered with 1.0 g of Tenax. This was heated to 180° C. for 10 minutes, and the Tenax was then extracted with diethyl ether before quantifying the photoinitiator present by HPLC.

Levels of photoinitiator vapour phase migration are shown in Table 2.

TABLE 2

Vapour phase migration results for thioxanthone photoinitiators

| Photoinitiator | Vapour phase migration onto Tenax (mg/m2) |
|---|---|
| ITX | 5.8 |
| Example 3 | <0.05 |

The results in Table 2 clearly demonstrate that the thioxanthone photoinitiator of Example 3 has a sufficiently low volatility to prevent any detectable vapour phase migration, in contrast, ITX has a significant vapour phase migration.

The invention claimed is:
1. Photoinitiator compounds of formula (I):

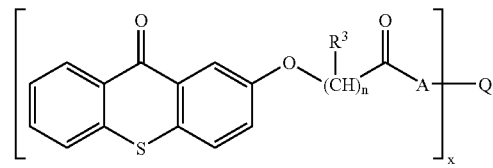

where: n is a number from 1 to 6;
R$^3$ represents a hydrogen atom, a methyl group or an ethyl group, and, when n is greater than 1, the groups or atoms represented by R$^3$ may be the same as or different from each other;
A represents a group of formula —[O(CHR$^2$CHR$^1$)$_a$]$_y$—, —[O(CH$_2$)$_b$CO]$_y$—, or —[O(CH$_2$)$_b$CO]$_{y-1}$—[O(CHR$^2$CHR$^1$)$_a$]—, where: one of R$^1$ and R$^2$ represents a hydrogen atom and the other represents a hydrogen atom, a methyl group or an ethyl group;
a is a number from 1 to 2;
b is a number from 4 to 5;
Q is a residue of ethylene glycol, propylene glycol, butylene glycol, glycerol, trimethylolpropane, di-trimethylolpropane, pentaerythritol or di-pentaerythritol;
x is a number greater than 1 but no greater than the number of available hydroxyl groups in Q; and
when x is a number greater than 1 but no greater than 2, y is a number from 1 to 10; or when x is a number greater than 2, y is a number from 3 to 10
and esters thereof in which a free hydroxyl group in Q has been esterified.

2. Compounds according to claim 1, in which n is 1.
3. Compounds according to claim 2, in which R$^3$ represents a hydrogen atom.
4. Compounds according to claim 1, in which n is a number from 2 to 6 and one group R$^3$ represents a hydrogen atom, or a methyl or ethyl group and the other or others of R$^3$ represent hydrogen atoms.
5. Compounds according to any one of claims 1 or 2 to 4, in which y is a number from 3 to 10.
6. Compounds according to any one of claims 1 or 2 to 4, in which A represents a group of formula —[OCH$_2$CH$_2$]$_y$—, —[OCH$_2$CH$_2$CH$_2$CH$_2$]$_y$— or —[OCH(CH$_3$)CH$_2$]$_y$—, where y is a number from 3 to 10.
7. Compounds according to any one of claims 1 or 2 to 4, in which A represents a group of formula —[O(CHR$^2$CHR$^1$)$_a$]$_y$— or —[O(CH$_2$)$_b$CO]$_{y-1}$—[O $(CHR^2CHR^1)_a]$—, where as is a number up to 2, b is a number from 4 to 5 and y is a number from 3 to 10.

8. Compounds according to any one of claims 1 or 2 to 4, in which x is 2 and y is a number from 1 to 10.

9. Compounds according to any one of claims 1 or 2 to 4, in which y is a number from 3 to 6.

10. Compounds according to claim 1, in which the residue $Q\text{-}(A\text{-})_x$ has a molecular weight no greater than 800.

11. An energy curable liquid composition, comprising: (a) a polymerizable component which is at least one ethylenically unsaturated monomer or oligomer; and (b) a photoinitiator according to any one of claims 1 or 2 to 4.

12. An energy curable liquid composition according to claim 11, which is a printing ink.

13. A process for preparing a cured polymeric composition by exposing a composition according to claim 11 to radiation.

14. A process according to claim 13, in which the radiation is ultraviolet.

15. An energy curable liquid composition, comprising:

(a) a polymerizable component which is at least one ethylenically unsaturated monomer or oligomer; and
(b) a photoinitiator according to claim 1 in which x is at least 2.

16. A process for preparing a cured polymeric composition by exposing a composition according to claim 15 to radiation.

\* \* \* \* \*